United States Patent [19]
Leue

[11] Patent Number: 5,986,188
[45] Date of Patent: Nov. 16, 1999

[54] BICOLOR IMPATIENS

[75] Inventor: Ellen Leue, DeKalb, Ill.

[73] Assignee: Pan America Seed Company, West Chicago, Ill.

[21] Appl. No.: 08/868,532

[22] Filed: Jun. 4, 1997

[51] Int. Cl.$^6$ .............................. A01H 5/00; A01H 1/04

[52] U.S. Cl. ...................... 800/323; 800/298; 800/260; Plt./317

[58] Field of Search .................................. 800/200, 205, 800/298, 323, 260; 47/58, DIG. 1; Plt./87.6, 317

[56] References Cited

U.S. PATENT DOCUMENTS

| | | | |
|---|---|---|---|
| P.P. 5,612 | 12/1985 | Hope | Plt./68 |
| P.P. 9,603 | 7/1996 | Leue | Plt./87.6 |
| P.P. 9,618 | 8/1996 | Leue | Plt./87.6 |
| 5,399,798 | 3/1995 | Drewlow et al. | 800/200 |

OTHER PUBLICATIONS

Ball Seed Catalog. From website:www.ballseed.com, 1998.
Goldsmith Seed Catalog. From website:www.goldsmith.com, 1998.
Hatterman–Valenti et al. Effect of 2,4–D and triclopyr on annual bedding plants. Journal of Environmental Horticulture, vol. 13, No. 3, pp. 122–125, (Abstract only), 1995.
RHS Dictionary of Gardening, Huxley [Ed.]. Impatiens entry, pp. 649–651. The MacMillan Press, London, 1992.

*Primary Examiner*—Douglas W. Robinson
*Assistant Examiner*—Melissa L. Kimball
*Attorney, Agent, or Firm*—Foley & Lardner

[57] ABSTRACT

Conventional *I. wallerana* bicolor petal patterns, such as the "star" and "picotee" patterns are polygenic in nature. Consequently, the color patterns are often lost or diluted when merged with other desirable polygenic traits. The novel stardust pattern, however, exhibits an exceptionally high degree of stability from flower to flower, and appears to be controlled by a single recessive gene. This simple inheritance allows the production of *I. wallerana* plants having the stardust trait with a variety of additional desirable characteristics.

9 Claims, 4 Drawing Sheets

(4 of 4 Drawing Sheet(s) Filed in Color)

BICOLOR IMPATIENS

BACKGROUND OF THE INVENTION

1. Field of the Invention

The present invention relates to Impatiens plants having a bicolor petal pattern that is stable from flower to flower and is inherited in a predictable manner. In particular, this invention is directed to *Impatiens wallerana* exhibiting the novel stardust trait. The present invention also is directed to methods for introgressing the gene that controls the stardust trait into a variety of genetic backgrounds. The present invention is further directed to methods for testing whether a particular Impatiens plant carries the stardust gene.

2. Background

Impatiens is primarily an Old World genus of flowering plants, with species distributed throughout tropical Africa, India, South-West Asia, southern China, Japan, and spreading into the north temperate zones of Europe, Russia, China and North America. In general, see Grey-Wilson, IMPATIENS OF AFRICA (A. A. Balkema 1980), and Nehrling et al., THE PICTURE BOOK OF ANNUALS (Hearthside Press, Inc. 1966). The family Balsaminaceae contains the monotypic Hydrocera and the prolific Impatiens, commonly referred to as the Balsams. Balsams are among the most decorative plants in cultivation. Moreover, most of the species are easily grown and can flower over a long period. The Balsam family includes three species grown as annuals in gardens: *I. balsamina, I. hawkerii,* and *I. wallerana.*

*I. wallerana* is an extremely variable species with a wide distribution in central east Africa. This species has also migrated into or naturalized in many of the moist tropical areas of the world. *I. wallerana* is probably the most commonly grown species of Impatiens and is cultivated in many parts of the world. In the trade, *I. wallerana* is frequently referred to as *I. sultani* or *I. holstii,* and may be commonly called "Busy Lizzy," "Patient Lucy," "Patience Plant," or "Sultana."

*I. wallerana* characteristically has two-flowered inflorescences and bright green, somewhat translucent leaves. The inflorescence may occasionally be one-flowered or three-flowered, and sometimes as many as five-flowered. The usual two-flowered structure shows a reduction in that there are frequently several tiny additional bracts, or even aborted buds, above the uppermost flowers. In the one-flowered form, there are always additional bracts.

The flowers of *I. wallerana* are typically rather flat, with a large upper (dorsal) petal and lateral petals almost equal in size and shape that are fused together at the base. The species can be obtained in a variety of colors ranging from pink to orange, red, mauve, purple and white.

Two well-known color patterns in *I. wallerana* have been designated as "star" and "picotee." The star trait is characterized by a white strip that runs down each petal, while petals with the picotee pattern have a basic color with margins of a second color. Since these traits are polygenic, it is difficult to transfer the star or picotee pattern into other genetic backgrounds. In attempts to merge these traits with other desirable polygenic characteristics, the color pattern is often lost or diluted. Accordingly, multiple complex crosses are necessary to improve other polygenic traits. The result is that commercial picotee and star hybrids often have persistent habit, seed quality or other performance problems.

Therefore, a need exists for a means to control Impatiens flower color in a predictable manner within a variety of desirable genetic backgrounds.

SUMMARY OF THE INVENTION

Accordingly, it is an object of the present invention to provide a method for breeding Impatiens plants that predictably exhibit a bicolor petal pattern.

It is a further object of this invention to provide Impatiens plants having a novel flower color pattern that is controlled by a single gene.

These and other objects are achieved, in accordance with one embodiment of the present invention, by the provision of an Impatiens plant that has flowers comprising bicolor petals, wherein each petal exhibits the stardust trait, which is a color pattern characterized by (a) a white central area, (b) a pigmented petal border, and (c) a transition zone located between the central area and the pigment border, wherein the transition zone comprises graded pigmented stippling. A suitable Impatiens plant is an African Impatiens plant.

Such Impatiens plants have an additional trait selected from the group consisting of compact plant habit, vigorous plant habit, deep green foliage, deep bronze foliage, light bronze foliage, glossy foliage, continuous flowering, large flowers, heavy flowering, full double flowers, semi-double flowers, segregating full double and semi-double flowers, drought tolerance, tolerance to full sun, flowers with flat rounded and overlapping petals, sheen on petals, pink-colored flowers, rose-colored flowers, salmon-colored flowers, orange colored-flowers, scarlet-colored flowers, red-colored flowers, lavender-colored flowers, violet-colored flowers, burgundy-colored flowers and intermediate shades.

The present invention also contemplates a method of producing an Impatiens plant having the stardust trait, comprising the steps of (a) crossing a first Impatiens plant that exhibits the stardust trait with a second Impatiens plant that does not exhibit the stardust trait to produce hybrids, and (b) breeding the hybrids to obtain F2 progeny that exhibit the stardust trait. Step (b) of such a method can be effected by self-pollinating the hybrids. Alternatively, step (b) can be performed by intercrossing the hybrids.

Such methods can be performed with a second Impatiens plant that exhibits at least one additional desired trait to produce F2 progeny that also exhibit one or more traits in addition to the stardust trait. Examples of such additional traits include compact plant habit, vigorous plant habit, deep green foliage, deep bronze foliage, light bronze foliage, glossy foliage, continuous flowering, large flowers, heavy flowering, full double flowers, semi-double flowers, segregating full double and semi-double flowers, tolerance to full sun, flowers with flat rounded and overlapping petals, sheen on petals, pink-colored flowers, rose-colored flowers, salmon-colored flowers, orange colored-flowers, scarlet-colored flowers, red-colored flowers, lavender-colored flowers, violet-colored flowers, and burgundy-colored flowers.

The present invention further contemplates methods for determining whether a test Impatiens plant carries the stardust gene, comprising the steps of (a) crossing the test plant with a control Impatiens plant that exhibits the stardust trait, and (b) observing the petal color pattern of the progeny of the cross, wherein the presence of the stardust trait in the progeny indicates that the test plant carries the stardust gene. Such methods can be performed in which at least one of the test Impatiens plant and the control Impatiens plant is an African Impatiens plant. Alternatively, the method can be performed in which both the test Impatiens plant and the control Impatiens plant are African Impatiens plants.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

DETAILED DESCRIPTION

1. Overview

Figure 1:
FIG. 1 shows flowers from *I. wallerana* cultivar No. 5125 displaying the stardust pattern.

Endeavors to merge particular color pattern traits with other desirable polygenic characteristics in *I. wallerana* have been excruciatingly slow and laborious. As described herein, however, the inventors have derived a novel flower color pattern from a wild accession of *I. wallerana*. Surprisingly, this new pattern, designated as "stardust," is controlled by a single recessive gene. Thus, unlike other novel color patterns in Impatiens, the stardust pattern is simply inherited, which provides a predictable transfer into a variety of genetic backgrounds, such as dark foliage, large flowered, or double-flowered forms.

The simple inheritance of the stardust pattern also provides a solution to problems that are linked or associated with commercial star patterns, including poor germination, small seed, unstable pattern, lateness to flower, poor flowering, small flowers, and poor branching, and problems associated with commercial picotee varieties, such as poor germination, light foliage color, poor flowering, cupped flowers, and disease susceptibility. Moreover, it is possible to take the parents of a successful solid colored variety that expresses none of these problems and backcross the stardust trait into the two parents separately, alternating backcrossing and self-pollination.

As an illustration, the stardust gene has been successfully integrated into dark foliage lines. In contrast, attempts to integrate the conventional star pattern with the dark foliage trait have not been successful due to low recovery of the star pattern and dark foliage in the same plant.

2. Discovery and Characterization of the Stardust Trait

The inventor obtained cuttings of plants found growing in the wild. The cuttings grew into very tall lanky plants with small flowers, which is typical of wild *I. wallerana*. Among the material were plants with light red, violet or light orange flowers, each with a small white "star" in the center of every flower. The image of a star was created by the presence of a near-white stripe, which ran down each petal.

These original wild collections were horticulurally unacceptable because they were tall, late to flower, had very small cupped flowers, and were available only the three colors. Moreover, the violet and orange flowered plants produced only a small amount of self seed, while the red plant failed to produce pollen.

In one study, the self seed of the violet and orange-flowered plants were sown and then selected two months later. Plants from both sets of seeds were basically true to type. One plant having orange flowers was potted and designated as "373-1".

A cross was performed between 373-1 and 313-1-2-1, a compact, large flowered, free flowering Impatiens line with solid violet-colored flowers. The cross was performed in an attempt to transfer the star pattern of the wild *I. wallerana* to a different genetic background. Crossing was performed by applying pollen from one plant directly to the exposed stigma of the flower of another plant (i.e., flower to flower pollination).

One hybrid, designated as "409-1", was noted to be a very vigorous, loose habit (poorly branched) with small solid cherry (between rose and red) colored flowers. There was no evidence of any pattern on the flowers. This was an unexpected observation because, often when a conventional star pattern is crossed with a solid-colored plant, the tips of the petals of the hybrid will be white. However, the new star pattern of the wild *I. wallerana* appeared to be completely recessive.

Self-pollinated progeny of 409-1 were sown and evaluated to characterize further the novel color pattern. Unique bicolors in violet, red, coral and rose segregated at a ratio of about three solid color to one bicolor. The latter contained "internal stars" in which each petal was bordered by pigment, with the white central area grading into the pigmented petal edge with an area of pigment stippling. The stippled transition area was broad in some plants, giving an overall "dusty" pattern. In certain plants, the transitional area was small, giving the impression of a conventional star pattern. In all cases, however, the pattern was very stable from flower to flower, which is unlike conventional star patterns. The new pattern was designated as "stardust".

Accordingly, the term "stardust trait" as used herein refers to a characteristic of bicolor flower petals, in which each petal has a color pattern having three zones: (1) a white central area, (2) a pigmented petal border, and (3) a transition zone located between the central area and the border, which contains graded pigmented stippling. See FIGS. 1 and 2.

Figure 3:
FIG. 3 shows a conventional star pattern in flowers from the commercial hybrid of Accent Orange Star.
Figure 4:
FIG. 4 shows a conventional star pattern in flowers from the commercial hybrid of Accent Red Star.

In contrast, conventional star patterns have a white stripe running to the edge of the petal, so that the pigmented border is broken by the white area. See FIGS. 3 and 4. Sometimes, there is a transitional area between the white and pigmented areas, but it shows diluted pigment rather than stippling. Also, the pattern is more or less unstable depending on the variety, and varies among plants within a variety as well as among flowers of a single plant. Often, the shape, size and percent of the white area within a flower will vary significantly, and will change according to temperature, nutrition and unknown factors.

Additional crosses were performed to introduce further improvements in plants having the stardust trait. In these studies, three selections, 409-1-1, 409-1-2, and 409-1-3, were crossed with a range of large-flowered, floriferous, compact hybrids, as shown in Table 1.

TABLE 1

| Parents | | Designation of Resulting |
|---|---|---|
| Female | Male | Family |
| 409-1-1 | 463-1 | 562 |
|  | 466-1 | 563 |
|  | 319-1-2-3-1 | 573 |
|  | 7565 | 603 |
|  | 253 | 637 |
| 409-1-2 | 471-1 | 564 |
|  | 389-1-1 | 576 |

TABLE 1-continued

| Parents | | Designation of Resulting |
|---|---|---|
| Female | Male | Family |
| 409-1-3 | 399-2-1 | 577 |
|  | 394-1-7 | 586 |
|  | 494-1 | 592 |
|  | 27-2-2-1 | 609 |
| 558-1 | 552-1 | 596 |

Families 573, 576, 577 and 609 were produced to incorporate the stardust trait into a dark foliage (heavily pigmented with anthocyanins) series. Because conventional star and picotee patterns are highly polygenic and currently in green foliage backgrounds, progress in breeding the color patterns into dark background, which is also polygenic, has been very slow. The single locus nature of the stardust trait, however, made it comparatively simple to combine with polygenic traits such as dark bronze foliage.

All families listed in Table 1 produced only solid flower color hybrids in the F1 generation, confirming the recessive nature of the stardust trait. The F2 generation of families 563 (selfs of four F1 selections), 564 (selfs of two selections), 573 (selfs of two selections), 576 (one self) and 577 (selfs of two selections) were sown and evaluated. All families segregated as about 25% stardust in a wide range of colors, with variation in the amount of pigment stippling. Three families were scored for the trait, with an aggregate number of 61 stardust and 270 solid color. All stardust segregants had clearly marked patterns. No intermediate or unstable patterned plants were found. These families had been put through several selective screenings for seed size and germination rate, suggesting that there may have been a distant linkage to less desirable alleles for these polygenic traits.

In one study, an additional three F2 families were sown and evaluated. Aggregate segregation was 68 stardust and 281 solid, again indicating the recessive nature of the stardust trait. As used herein, the term "stardust gene" refers to the gene that produces this recessive stardust trait.

Through intercrossing wild stardust plants with cultivated breeding material, followed by growing the plants to maturity and selecting the desired progeny plants, it was possible to make very rapid progress in the transfer of the stardust gene into various horticultural backgrounds. For example, it has been possible to incorporate smaller leaves, improved earliness to flower, and a desirable flower-to-plant ratio.

As an illustration, the original wild collections flowered in 61 days (violet) and 67 days (orange) from a May sowing, while cultivated *I. wallerana* breeding material averaged 50 days to flower. This original *I. wallerana* material was crossed with a very early, compact selection and the F1 flowered in 56 days from an October sowing, compared with an average of 52 days for cultivated breeding crosses. Further progress was made with an additional cross of F2 selections to cultivated material, so that families having 75% of their genes from cultivated and 25% of their genes from the wild stardust accession are indistinguishable for earliness from normal breeding lines. The breeding experiments presented in Example 1 further illustrate the production of hybrids that carry the stardust gene and manifest additional desired traits.

In sum, breeding studies revealed that a sample of wild *I. wallerana* had a stable star pattern that provided an exceptionally high degree of stability from flower to flower and a unique pigment stippling pattern in hybrids. The stardust trait appears to be controlled by a single recessive gene, which allows the production of *I. wallerana* plants having the stardust trait with a variety of additional desirable characteristics.

3. Production of Bicolor *I. wallerana* Plants Exhibiting the Stardust Trait

Plants having the stardust trait can be used to introgress the stardust gene into various genetic backgrounds. Desirable traits include compact plant habit, vigorous plant habit, well-branched plants, deep green foliage, deep bronze foliage, light bronze foliage, glossy foliage, continuous flowering, large flowers, heavy flowering, early to flower, full double flowers, semidouble flowers, segregating full double and semidouble flowers, whitish leaf variegation, yellowish leaf variegation, drought tolerance, tolerance to full sun, excellent flower form with flat rounded overlapping petals, sheen on petals, large seed size, excellent germination with seedling vigor and uniformity, and full color range, including all shades of pink, rose, salmon, orange, scarlet, red, lavender, violet, burgundy, and intermediate shades. Well-known Impatiens plants having such characteristics are readily available. For example, Dazzler Blush has a compact plant habit, Super Elfin White has deep green foliage, and Deco Salmon has deep bronze foliage.

African Impatiens plants having the stardust trait can be bred with African Impatiens exhibiting additional desirable characteristics. For example, *I. wallerana, I. usambarensis, I. cinnabarina,* and *I. niamniamensis* can be cross bred to produce hybrids with the stardust trait and at least one other desirable trait. African Impatiens can also be crossed with New Guinea Impatiens to produce hybrids with desired traits. An example of a suitable species of New Guinea Impatiens is *I. hawkerii*. Additional suitable species of Impatiens include *I. auricoma, I. hookeriana, I. epiphytica,* and *I. uguenensis*.

Introgression of the stardust gene into a desired genetic background can be performed by applying pollen from one plant to the exposed stigma of the flower of another plant. Alternatively, introgression can be achieved by standard methods of protoplast fusion.

After obtaining Impatiens that have a desired blend of traits, the plants can be propagated using standard methods. For example, Impatiens plants are readily grown from cuttings, as described in Appendix 2 of Grey-Wilson, IMPATIENS OF AFRICA (A. A. Balkema 1980). In fact, Impatiens plants are so easily propagated from cuttings that they will root readily in a jar of water.

As an example, a cutting is made about 8–14 cm long from young healthy shoots, incising the stem immediately below a node.

Cuttings should be chosen to include nodes with at least one vegatative branch or axillary vegetative meristem. The cuttings are placed in a warm propagating frame or in a pot and exposed to indirect sunlight. These will root in about ten days. Plants in cultivation are healthiest in temperatures between 18–25° C.

*I. wallerana* is also easily raised from seed. See, for example, DeWolf, Jr. (ed), TAYLOR'S GUIDE TO ANNUALS, page 344 (Houghton Mifflin Co. 1986). Seedlings grow rapidly and may be in flower within two months of sowing. It should be noted that, although Impatiens have perfect flowers, the plants are strongly protandrous and seldom produce self-pollinated seed on their own. Accordingly, self seed is obtained by manual pollination, as described above.

Since the stardust pattern appears to be controlled by a single recessive gene, it is possible to determine whether a particular plant carries the stardust gene by performing an allelism test. This test is performed by crossing the test plant with a plant exhibiting the stardust trait. If the product of the cross also has the stardust trait, then the test plant carries the stardust gene. On the other hand, if all hybrid progeny have a solid color, then the star-like pattern of the test plant is not due to the stardust gene.

As an illustration, three Impatiens color patterns are star, picotee and mosaic (Goldsmith Seeds Inc.; Gilroy, Calif.). When a plant having the stardust trait is crossed with plants having any of these conventional traits, the hybrids have solid colors.

The present invention, thus generally described, will be understood more readily by reference to the following examples, which are provided by way of illustration and are not intended to be limiting of the present invention. Color references are based on a Pantome PMS color number.

EXAMPLE 1

Introgression of the Stardust Gene

Breeding studies were performed with plants derived from self seed of the original stardust violet accession (558.2) and various cultivated lines. Table 2 compares certain features of the parent 558.2 plants with three F2 selections. The results show that it is possible to obtain hybrids containing the stardust gene that exhibit additional desired traits, such as the flat open flower form.

TABLE 2

| Designation | Flower Color | Plant Height (cm) | Individual Flower Breadth (cm) | Total Flower Area (cm)$^2$ | Flower Shape | Stem Length (cm) |
| --- | --- | --- | --- | --- | --- | --- |
| 558.2 (parent from original wild collection) | violet | 21 | 3.2 | 20.56 | slightly cupped to fully cupped | 28 |
| 409.1.4 | violet | 8 | 4.5 | 41.43 | flat open | 8 |
| 409.1.5 | light cherry | 7 | 4.2 | 37.75 | flat open | 9 |
| 409.1.6 | light cherry | 9 | 4.2 | 37.75 | flat open | 14 |

Another study examined the results of combining the stardust trait with semi-doubleness. Impatiens plants typically have five petals per flower, which is referred to as the "single-type" or "singleness" trait. In contrast, the "semi-double" characteristic refers to flowers that have six to ten partial or full petals.

Table 3 shows that the stardust trait appeared in about 20% of 1634 plants scored. Segregation of the semidouble trait indicates control by a single recessive gene. The amount of petalage, indicated by the arbitrary delineations of "poor" and "good" semidoubling, appears to be polygenic.

TABLE 3

| Color Pattern | Single | Poor Semi-double | Good Semi-double | Sum |
| --- | --- | --- | --- | --- |
| Solid | 1021 (62.5%) | 195 (11.9%) | 75 (4.6%) | 1291 |

TABLE 3-continued

| Color Pattern | Single | Poor Semi-double | Good Semi-double | Sum |
| --- | --- | --- | --- | --- |
| Stardust | 257 (15.7%) | 62 (3.8%) | 24 (1.5%) | 343 |

EXAMPLE 2

Breeding of *I. wallerana* Cultivar No. 5125

Figure 2:
FIG. 2 shows flowers from *I. wallerana* cultivar No. 5126 displaying the stardust pattern.

*I. wallerana* Cultivar No. 5125 was bred by crossing selection 576-1-2 as the female with selection 563-1-1 as the male. Selection 576-1-2 produces stardust violet (2405C) flowers, green foliage and is propagated by cuttings. Selection 563-1-1 produces stardust red (206C) flowers, foliage with light spots of anthocyanin on the underside of the leaves and is propagated by cuttings. The hybrid Cultivar No. 5125 produces stardust-type flowers segregating petal edge color rose (226C), violet (2405C), cherry red (Pantone rubine red) and burgundy (227). Additionally, hybrid Cultivar No. 5125 has very light spots of pigment on the underside of the leaves. Flowers from a selection of this cultivar are shown in FIG. 1. Seeds of hybrid cultivar No. 5125 were deposited on May 6, 1997 in the American Type Culture Collection, 12301 Parklawn Drive, Rockville, Md. 20852 and accorded accession No. 209017.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention, which is defined by the following claims.

All publications and patent applications mentioned in this specification are indicative of the level of skill of those in the art to which the invention pertains. All publications and patent applications are herein incorporated by reference to the same extent as if each individual publication or patent application were specifically and individually indicated to be incorporated by reference in its entirety.

What is claimed is:

1. An *Impatiens wallerana* plant that has flowers comprising bicolor petals, wherein each petal exhibits the stardust trait, which is a color pattern characterized by (a) a white central area, (b) a pigmented petal border, and (c) a transition zone located between said central area and said pigment border, wherein said transition zone comprises graded pigment stippling, and said stardust trait is controlled by a single recessive gene.

2. The plant of claim 1, wherein said plant additionally exhibits at least one trait selected from the group consisting of compact plant habit, vigorous plant habit, deep green foliage, deep bronze foliage, light bronze foliage, glossy foliage, continuous flowering, large flowers, heavy flowering, full double flowers, semi-double flowers, segregating full double and semi-double flowers, tolerance to full sun, flowers with flat rounded and overlapping petals, sheen on petals, pink-colored flowers, rose-colored flowers, salmon-colored flowers, orange colored-flowers, scarlet-colored flowers, red-colored flowers, lavender-colored flowers, violet-colored flowers, and burgundy-colored flowers.

3. A method of producing the plant of claim 1, comprising the steps of:

(a) crossing a first *Impatiens wallerana* plant that exhibits said stardust trait with a second *Impatiens wallerana* plant that does not exhibit said stardust trait to produce hybrids, and (b) breeding said hybrids to obtain F2 progeny that exhibit said stardust trait.

4. The method of claim 3, wherein said breeding step is effected by self-pollinating said hybrids.

5. The method of claim 3, wherein said breeding step is effected by intercrossing said hybrids.

6. The method of claim 3, wherein said F2 progeny exhibit the stardust trait and at least one additional trait that is also exhibited by said second plant, wherein said additional trait is selected from the group consisting of compact plant habit, vigorous plant habit, deep green foliage, deep bronze foliage, light bronze foliage, glossy foliage, continuous flowering, large flowers, heavy flowering, full double flowers, semi-double flowers, segregating full double and semi-double flowers, tolerance to full sun, flowers with flat rounded and overlapping petals, sheen on petals, pink-colored flowers, rose-colored flowers, salmon-colored flowers, orange colored-flowers, scarlet-colored flowers, red-colored flowers, lavender-colored flowers, violet-colored flowers, and burgundy-colored flowers.

7. A method for determining whether a test *Impatiens wallerana* plant carries the stardust gene, said method comprising the steps of:

(a) crossing said test plant with a control *Impatiens wallerana* plant that exhibits the stardust trait, and (b) observing the petal color pattern of the progeny of said cross, wherein the presence of the stardust trait in said progeny indicates that said test plant carries the stardust gene.

8. A plant part obtained from the impatiens plant of claim 1.

9. The plant part of claim 8, wherein said plant part is select from the group consisting of propagated cuttings, seeds and pollen.

* * * * *